(12) United States Patent
Gill et al.

(10) Patent No.: US 7,783,348 B2
(45) Date of Patent: Aug. 24, 2010

(54) STIMULATION DEVICE FOR TREATING OSTEOARTHRITIS (75) Inventors: Jagjit Gill, Rochester, MN (US);
Kin-Joe Sham, Shoreview, MN (US);
Bryan Armitage, Stillwater, MN (US)

(73) Assignee: OrthoCor Medical, Inc., Minneapolis, MN (US)

( * ) Notice: Subject to any disclaimer, the term of this patent is extended or adjusted under 35 U.S.C. 154(b) by 9 days.

(21) Appl. No.: 12/104,007

(22) Filed: Apr. 16, 2008

(65) Prior Publication Data

US 2008/0288035 A1 Nov. 20, 2008

Related U.S. Application Data (60) Provisional application No. 60/927,354, filed on May 3, 2007, provisional application No. 60/983,653, filed on Oct. 30, 2007.

(51) Int. Cl.
*A61N 1/18* (2006.01)
(52) U.S. Cl. .................... 607/3; 602/2; 600/15
(58) Field of Classification Search .......... 607/3, 607/50, 2, 51; 602/2; 600/13, 15
See application file for complete search history.

(56) References Cited

U.S. PATENT DOCUMENTS

| 4,240,445 A | 12/1980 | Iskander et al. |
| 4,256,116 A | 3/1981 | Meretsky et al. |
| 4,412,540 A | 11/1983 | Bentall |
| 4,548,208 A | 10/1985 | Niemi |
| 4,674,482 A | 6/1987 | Waltonen et al. |
| 4,727,857 A | 3/1988 | Horl |
| 4,757,804 A | 7/1988 | Griffith et al. |
| 4,886,063 A | 12/1989 | Crews |

(Continued)

FOREIGN PATENT DOCUMENTS

WO 2004069128 8/2004

(Continued)

OTHER PUBLICATIONS

Fini et al., "Effects of pulsed electromagnetic fields on articular hyaline cartilage: review of experimental and clinical studies," Biomedicine & Pharmacotherapy 59 (Feb. 2005) 388-394.

(Continued)

*Primary Examiner*—Carl H Layno
*Assistant Examiner*—Pamela M Bays
(74) *Attorney, Agent, or Firm*—Schwegman, Lundberg & Woessner, P.A.

(57) ABSTRACT

A device for providing therapeutic treatment to a body part such as a knee joint to promote healing of the body part, including a signal generator for generating a pulsed electromagnetic field to electromagnetic stimulators based upon a selected treatment mode, a controller for storing the treatment mode and communicating the treatment mode to the signal generator and stimulators, a heat source configured to provide thermal therapy to the body part, and a monitoring element for monitoring the electromagnetic field generated by the electromagnetic stimulators. The device may also include a telemetry component in communication with the monitor for remotely accessing the controller to modify the treatment mode. The device can also be disposable.

25 Claims, 8 Drawing Sheets

U.S. PATENT DOCUMENTS

| | | | |
|---|---|---|---|
| 4,989,604 A | 2/1991 | Fang | |
| 5,000,178 A | 3/1991 | Griffith | |
| 5,014,699 A | 5/1991 | Pollack et al. | |
| 5,181,902 A | 1/1993 | Erickson et al. | |
| 5,314,401 A | 5/1994 | Tepper | |
| 5,336,255 A | 8/1994 | Kanare et al. | |
| 5,401,233 A | 3/1995 | Erickson et al. | |
| 5,411,542 A | 5/1995 | Jensen | |
| 5,478,303 A | 12/1995 | Foley-Nolan et al. | |
| 5,487,759 A | 1/1996 | Bastyr et al. | |
| 5,578,065 A | 11/1996 | Hattori et al. | |
| 5,584,863 A | 12/1996 | Rauch et al. | |
| 5,718,721 A | 2/1998 | Ross | |
| 5,723,001 A | 3/1998 | Pilla et al. | |
| 5,743,844 A | 4/1998 | Tepper et al. | |
| 5,860,945 A * | 1/1999 | Cramer et al. | 602/62 |
| 5,922,012 A | 7/1999 | Sakano | |
| 5,947,913 A | 9/1999 | Palumbo | |
| 5,951,459 A | 9/1999 | Blackwell | |
| 6,024,691 A | 2/2000 | Tepper et al. | |
| 6,042,531 A | 3/2000 | Holcomb | |
| 6,096,067 A | 8/2000 | Cramer et al. | |
| 6,129,659 A | 10/2000 | Wilk | |
| 6,132,362 A | 10/2000 | Tepper et al. | |
| 6,186,941 B1 | 2/2001 | Blackwell | |
| 6,200,259 B1 | 3/2001 | March | |
| 6,213,934 B1 | 4/2001 | Bianco et al. | |
| 6,228,108 B1 | 5/2001 | Lamb et al. | |
| 6,261,221 B1 | 7/2001 | Tepper et al. | |
| 6,275,737 B1 | 8/2001 | Mann | |
| 6,334,069 B1 | 12/2001 | George et al. | |
| 6,353,763 B1 | 3/2002 | George et al. | |
| 6,436,020 B1 | 8/2002 | Weingand | |
| 6,443,883 B1 | 9/2002 | Ostrow et al. | |
| 6,463,336 B1 | 10/2002 | Mawhinney | |
| 6,465,709 B1 | 10/2002 | Sun et al. | |
| 6,506,403 B1 | 1/2003 | Yu | |
| 6,551,233 B2 | 4/2003 | Perreault et al. | |
| 6,561,968 B1 | 5/2003 | Dissing et al. | |
| 6,589,159 B2 | 7/2003 | Paturu | |
| 6,592,509 B1 | 7/2003 | Hunter, Jr. | |
| 6,606,519 B2 | 8/2003 | Powell | |
| 6,641,520 B2 | 11/2003 | Bailey et al. | |
| 6,675,047 B1 | 1/2004 | Konoplev et al. | |
| 6,678,562 B1 | 1/2004 | Tepper et al. | |
| 6,701,185 B2 | 3/2004 | Burnett et al. | |
| 6,839,595 B2 | 1/2005 | Tepper et al. | |
| 6,875,188 B2 | 4/2005 | Chiang | |
| 6,955,642 B1 | 10/2005 | Simon | |
| 7,008,369 B2 | 3/2006 | Cuppen | |
| 7,022,506 B2 | 4/2006 | Brighton et al. | |
| 7,087,076 B2 | 8/2006 | Purcell | |
| 7,130,692 B2 | 10/2006 | Brighton et al. | |
| 7,175,587 B2 | 2/2007 | Gordon et al. | |
| 7,215,995 B2 | 5/2007 | Brighton et al. | |
| 7,336,993 B1 | 2/2008 | Szeles | |
| 7,551,957 B2 | 6/2009 | Whelan et al. | |
| 2002/0143373 A1* | 10/2002 | Courtnage et al. | 607/91 |
| 2004/0010178 A1 | 1/2004 | Buckner | |
| 2004/0176803 A1 | 9/2004 | Whelan et al. | |
| 2004/0176805 A1 | 9/2004 | Whelan et al. | |
| 2004/0176806 A1 | 9/2004 | Markoll | |
| 2005/0049653 A1* | 3/2005 | Wang | 607/48 |
| 2005/0087194 A1* | 4/2005 | Scott | 128/846 |
| 2006/0190043 A1 | 8/2006 | Brighton et al. | |
| 2007/0167990 A1 | 7/2007 | Mangrum et al. | |
| 2008/0132971 A1 | 6/2008 | Pille et al. | |

FOREIGN PATENT DOCUMENTS

| | | | |
|---|---|---|---|
| WO | 2006096698 | | 9/2006 |
| WO | 2006115119 | | 11/2006 |
| WO | WO2006115119 | * | 11/2006 |
| WO | WO-2008137319 A1 | | 11/2008 |

OTHER PUBLICATIONS

Sutbeyaz et al., "The effect of pulsed electromagnetic of fields in the treatment of cervical osteoarthritis: a randomized, double-blink, sham-controlled trial," Rheumatol Int (Jan. 2006) 26:320-324.

International Search Report and Written Opinion of International application No. PCT/US2008/061214, mailed Jul. 8, 2008, 14 pp.

"CDRH Document Imaging System: Folder K903675", (Nov. 1992), 77 pgs.

"Ivivi SofPulse: Premarket Notification [501(k)] Summary", *Ivivi Technologies Inc.*, (Dec. 2008), 5 pgs.

"OrthoCor Active Knee System: Premarket Notification [501(k)] Summary", *Orthocor Medical, Inc.*, (Dec. 2009), 5 pgs.

\* cited by examiner

STIMULATION DEVICE FOR TREATING OSTEOARTHRITIS

CROSS-REFERENCE TO RELATED APPLICATION(S)

This application claims priority to U.S. Provisional Application 60/927,354, entitled Stimulation Device for Treating Osteoarthritis and filed on May 3, 2007, and further claims priority to U.S. Provisional Application 60/983,653, entitled Stimulation Device for Treating Osteoarthritis and filed on Oct. 30, 2007, the contents of both of which are hereby incorporated herein by reference in their entireties.

FIELD OF THE INVENTION

The methods and devices disclosed herein relate to methods and devices for treating osteoarthritis. More specifically, the devices and methods include the application of one or both of PEMF stimulation and thermal treatment to a target area.

BACKGROUND OF THE INVENTION

The various embodiments disclosed herein relate to devices and methods for the treatment of osteoarthritis. More particularly, the embodiments relate to portable, disposable pulsed electromagnetic field (PEMF) stimulation and thermal therapy devices for treating osteoarthritis and their methods of use.

Osteoarthritis, also known as degenerative joint disease, is characterized by gradual loss of hyaline cartilage and, in extreme cases, cyst formation in and deformation of the subchondral bone. The hyaline cartilage lines the articular surfaces of the knee and provides cushion and lubrication for the joint. During osteoarthritis, the extra-cellular matrix of the cartilage is worn down at a greater rate than it is being synthesized, leading to a net reduction in the overall amount of cartilage at the articular surfaces of the knee. As the cartilage breaks down, symptoms such as pain, swelling, tenderness, stiffness, and eventual muscle atrophy are manifested. Chondrocytes, the cellular component of hyaline cartilage that is responsible for matrix synthesis and turnover, are also depleted, thus resulting in an inability to naturally recover from this disease. Additionally, cells present in osteoarthritic joints release catabolic cytokines and enzymes that suppress collagen synthesis.

To date, conventional therapies for osteoarthritis have aimed at reducing pain and the progression of joint damage in order to minimize disability and maximize quality of life. The current algorithm for the management of osteoarthritis includes diagnosing the disease, modifying patient activity, prescribing anti-inflammatory medications, injecting steroids into the knee, and as a last resort, surgery. Although this regimen does provide some benefit, it is by no means a cure all for patients with osteoarthritis.

Aside from the conventional therapies, there are currently a number of alternative therapies that may be used to treat osteoarthritis. Three of the forerunners in the non-invasive alternative therapy field include electric, static magnetic, and electromagnetic stimulation.

Electrical stimulation, such as transcutaneous electrical nerve stimulation (TENS), delivers mild electrical impulses across the skin and into regional nerves. In patients having osteoarthritis, pain impulses are transmitted to the spinal cord through small cutaneous fibers. TENS acts to stimulate large cutaneous fibers that subsequently transmit a faster impulse via C-fibers to inhibit pain signals from the small fibers. It is in this way that TENS masks the pain normally experienced by patients having osteoarthritis. It is also thought that TENS incites the secretion of endogenous opiates, the body's natural pain killers, further reducing the pain experienced by patients with osteoarthritis.

Static magnetic stimulation has also been shown to provide medically relevant benefits. Various experiments designed to induce osteoporosis, fracture, and synovitis in animals have demonstrated faster bone repair, increased bone density, and decreased joint inflammation following magnetic treatments. It is thought that magnets can affect biological processes by: decreasing the firing rate of chronic pain neurons; modifying the rate of enzyme-mediated reactions; modulating intracellular signaling by affecting the functioning of calcium channels in the cell membranes; and enhancing blood flow. All of the above may provide some therapeutic benefit with respect to the symptoms of osteoarthritis.

Additionally, electromagnetic stimulation, a modality that generates a magnetic field by sending current through a coil, may also provide medical benefits for the treatment of osteoarthritis. It has been observed that physical stress on bone causes the appearance of tiny electric currents (piezoelectric potentials) that are thought to be the mechanism of transduction of the physical stresses into a signal that promotes bone formation. In particular, studies of electrical phenomena in cartilage have demonstrated a mechanical-electrical transduction mechanism resembling those described in bone, appearing when cartilage is mechanically compressed. Generating currents within cartilage is thought to stimulate chondrocyte activity, thus promoting the synthesis of cartilage. New cartilage synthesis may work to combat the degeneration seen in osteoarthritis and therefore alleviate the symptoms of osteoarthritis.

Thus, there is a need for an improved device and method to treat osteoarthritis.

BRIEF SUMMARY OF THE INVENTION

A portable, non-invasive device comprised of a multiple usage cuff and two single-use therapy units is designed to provide Electro-Magnetic Thermal Therapy ($EMT^2$) for treating knee osteoarthritis. The $EMT^2$ provides both transcutaneous pulsed electromagnetic field stimulation and thermal therapy. For purposes of this application, it is understood that "thermal therapy" means any therapy that provides for application of heat or cold for purposes of treatment. The $EMT^2$ is designed to alleviate pain and increase range of motion without requiring direct skin contact to the afflicted joint. The single-use therapy units offer heat or cooling and PEMF stimulation when inserted into the cuff, which provides the power and control for the coils. The cuff may contain a rechargeable power source capable of delivering a recommended amount of therapy and the coils for delivering the PEMF stimulation. The cuff may be fastened to the knee in a manner that directs the therapy to the medial and lateral areas of the joint. Furthermore, the cuff may be designed such that it is aesthetically pleasing and comfortable to wear during daily activities either over or underneath clothing, thereby increasing patient compliance.

The basic principle behind the concept of electromagnetic stimulation is that passing an electric current through a coil winding structure will generate an electromagnetic field. The electromagnetic field can, in turn, generate a current in any conductive material, such as nerves or other body tissues, within this field. The electromagnetically induced electric field created by properly oriented pulsed electromagnetic stimulation thus accomplishes the result of transferring charge to cells of the body. This induced current can lead to nerve firing, muscle contraction, stimulation of cell signaling pathways causing cell growth, and a number of other effects. In contrast to applications of electrical stimulation, pulsed electromagnetic stimulation does not require direct skin contact to induce nerve excitation. As a result, significantly higher levels of directed stimulation can be achieved through pulsed electromagnetic stimulation without the adverse effects of other technologies.

Thus, the $EMT^2$ devices and methods disclosed herein are designed with a powerful electromagnetic stimulating means created for the purpose of stimulating nerve, muscle, and/or other body tissues. Previous clinical studies have shown a high correlation between low-frequency PEMF and new cartilage growth for treating osteoarthritis. The inventive device provides an easy-to-use, portable system that may have applications within a host of clinical and home health applications.

DETAILED DESCRIPTION

Figure 1:
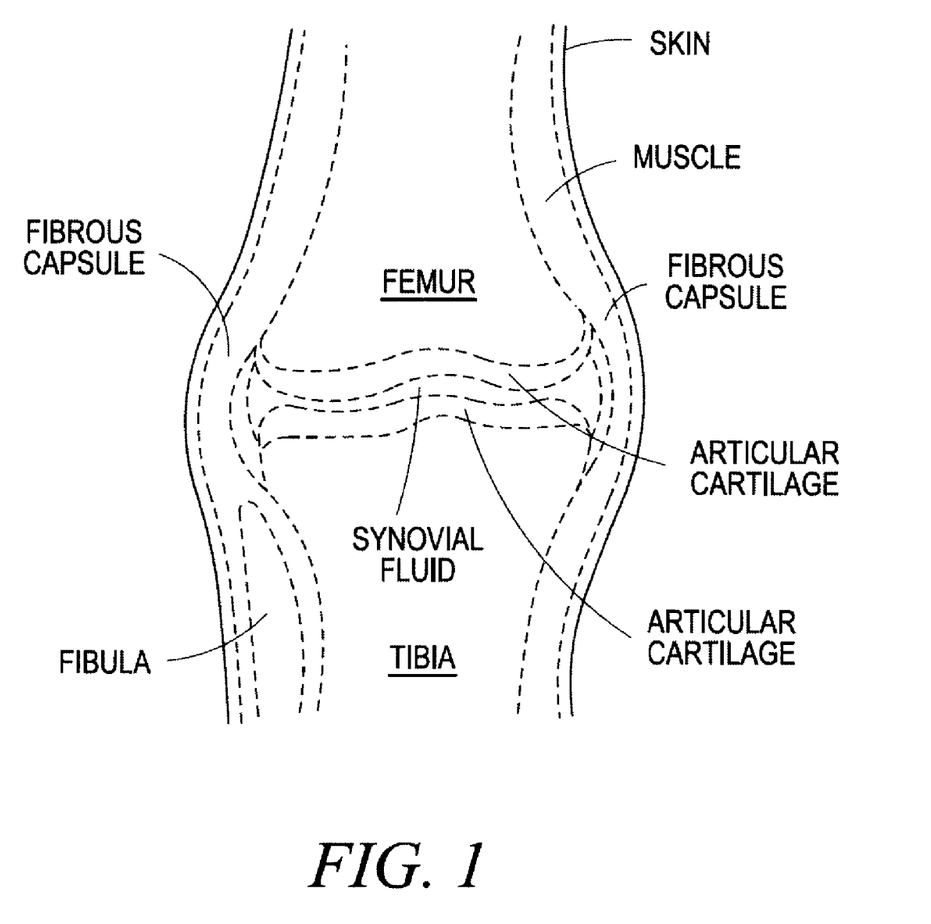
FIG. 1 is a diagram illustrating a typical human knee joint model.

FIG. 1 is a diagram illustrating a typical human knee joint model. As shown in FIG. 1, the typical human knee joint includes a compartment filled with synovial fluid that is bounded by articular cartilage on the ends of the femur and tibia, respectively, and fibrous capsules. In accordance with one embodiment of the devices and methods discussed herein, osteoarthritis in the knee joint may be treated by the application of heat or cold and specific and selective electromagnetic fields via coils positioned adjacent to the knee joint. As will be discussed in more detail to follow, a signal generator means may provide the appropriate signals to the coils for generating the specific and selective electromagnetic fields. The specific and selective electromagnetic field needed to treat osteoarthritis in the knee joint may be calculated, and varies depending upon, among other factors, the dimensions of the tibia and femur and the severity of the symptoms. Furthermore, a heating or cooling source may also be positioned adjacent to the knee joint to relieve pain, reduce patient discomfort, and increase range of motion. The heating or cooling source can also be referred to as a "thermal exchange component," which, for purposes of the instant application, means any component or device that can be used to apply heat (or any temperature that is higher than the patient's body temperature or the ambient temperature) or cold (or any temperature that is lower than the patient's body temperature or the ambient temperature).

More particularly, the implementations discussed herein relate to devices and methods for generating both (1) heat or cold, and (2) selective pulsed electromagnetic fields for the treatment of diseased tissue in a joint, such as a knee joint. The devices, which may be designed in numerous forms such as a knee brace or a small dermal patch, preferably offer transcutaneous stimulation for treating osteoarthritis. The devices may be designed to provide stimulation directly to the afflicted joint to alleviate pain and increase range of motion.

As will be discussed in further detail in subsequent paragraphs, the various $EMT^2$ stimulation device embodiments may be designed to attach to a patient for a prolonged period of time while having little disruption to daily activities and minimal skin irritation. In addition, the stimulation devices may be designed such that it is aesthetically pleasing and comfortable to wear. As a result of these and other design characteristics, patient refusal of treatment due to discomfort (i.e., patient "non-compliance") may be minimized.

Pulsed electromagnetic fields generate small, induced currents (Faraday currents) in the highly conductive extracellular fluid, which thereby mimics endogeneous electrical currents. The endogeneous electrical currents are due primarily to movement of fluid containing electrolytes in channels of the bone containing organic constituents with fixed negative charges, generating what are called "streaming potentials." Studies of electrical phenomena in cartilage have demonstrated a mechanical-electrical transduction mechanism that resembles those described in bone, appearing when cartilage is mechanically compressed, causing movement of fluid and electrolytes over the surface of fixed negative charges in the proteoglycans and collagen in the cartilage matrix. These streaming potentials serve a purpose in cartilage similar to that in bone, and, along with mechanical strain, lead to signal transduction that is capable of stimulating chondrocyte synthesis of matrix components.

In contrast to direct currents, PEMFs are able to penetrate cell membranes and either stimulate them or directly affect intracellular organelles. As a result, the effect of PEMFs on extracellular matrices includes increased synthesis of cartilage molecules, thereby enabling a "remodeling" of the knee joint.

Figure 2:
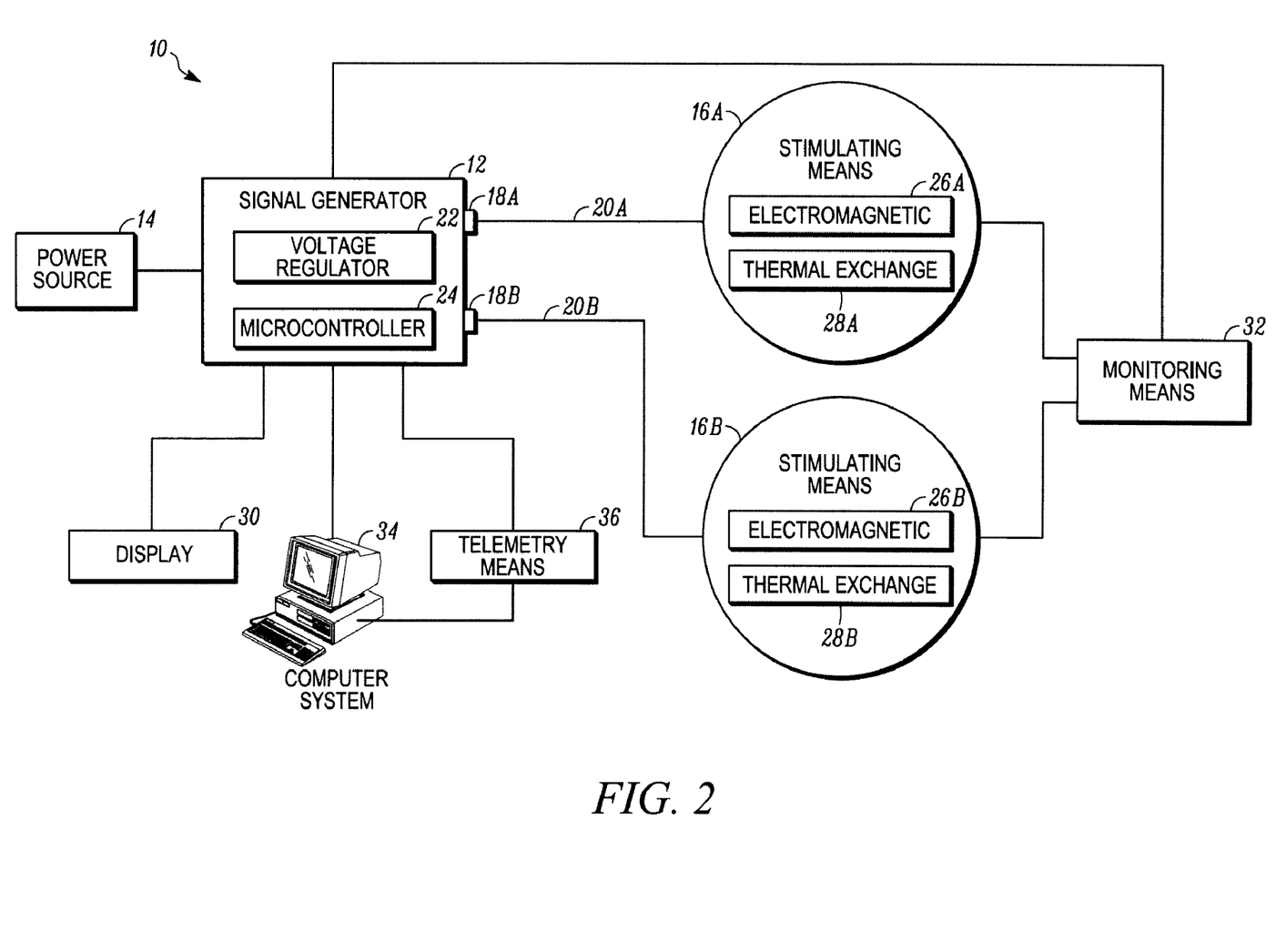
FIG. 2 is a block diagram illustrating a stimulation device for treating osteoarthritis in the knee according to one embodiment.

FIG. 2 is a block diagram illustrating $EMT^2$ stimulation device 10 for treating osteoarthritis in the knee according to one embodiment. This device embodiment 10 has a signal generator 12, power source 14, first stimulating means 16A, and second stimulating means 16B. First stimulating means 16A is coupled to first output 18A of signal generator 12 via first signal line 20A. Similarly, second stimulating means 16B is coupled to second output 18B of signal generator 12 via second signal line 20B. In various embodiments, the first stimulating means 16A has either or both of an electromagnetic stimulating means 26A and a thermal exchange component 28A and the second stimulating means 16B has either or both of an electromagnetic stimulating means 26B and a thermal exchange component 28B.

First and second signal lines 20A and 20B are configured to deliver the signals generated by signal generator 12 to create the appropriate therapeutic stimulation via first and second stimulating means 16A and 16B. First and second signal lines 20A and 20B may be "wired," such as with coaxial cable. Alternatively, a "wireless" connection means, such as Bluetooth, may be used.

Although stimulation device 10 is shown as having two output ports 18A and 18B for simultaneously and independently delivering output signals (either the same or different signals) to two stimulating means 16A and 16B, one skilled in the art will appreciate that the number of output ports and stimulating means may be varied without departing from the intended scope of the implementations disclosed herein. Thus, embodiments of device 10 that include any number of stimulating means are contemplated. For example, in one alternative embodiment, the device 10 can have one stimulating means.

Power source 14, which may be, for example, a lithium battery pack, is provided for delivering a current input to signal generator 12. While shown in FIG. 2 as a remote unit, power source 14 may be incorporated as part of or housed together with signal generator 12. Since the embodiments may be designed with low power requirements, power source 14 may be one capable of providing an average power input of less than about 300 mW per session. As a result, power source 14 is generally small and lightweight. In an alternative embodiment, the device 10 has two power sources—one to supply power to the signal generator and another to supply power to create the thermal exchange.

As shown in FIG. 2, signal generator 12 may include voltage regulator 22 and microcontroller 24. Furthermore, first stimulating means 16A may include first electromagnetic stimulating means 26A and first thermal exchange component 28A, while second stimulating means 16B may include second electromagnetic stimulating means 26B and second thermal exchange component 28B. In one embodiment, the first and second electromagnetic stimulating means 26A, 26B are first and second coils 26A, 26B. Voltage regulator 22 may be used to provide various required supply voltages to first and second electromagnetic stimulating means 26A and 26B. First and second electromagnetic stimulating means 26A and 26B may be triggered by microcontroller 24, which may be designed to generate accurate pulses at a particular triggering and switching frequency. Output signals are delivered from microcontroller 24 to first and second stimulating means 16A and 16B, each of which is individually responsive to the signals to create a pulsed electromagnetic field.

As shown in FIG. 2, alternative embodiments of the device 10 may further include display 30 and monitoring means 32. Display 30 may be designed to display many different treatment parameters, including but not limited to a treatment mode, a power level, and an amount of time remaining in a treatment session.

Monitoring means 32 may be designed for monitoring one or more of the output conditions of stimulation device 10. In particular, monitoring means 32 may be configured to ensure that accurate treatment dosages are delivered through first and second stimulating means 16A and 16B to the patient's knee. One condition that may be monitored by monitoring means 32 is the electromagnetic field generated by first and second coils 26A and 26B. In particular, monitoring means 32 may include circuitry to both detect the strength of the electromagnetic field and adjust the signals delivered to the coils if the sensed field is not in accordance with the desired treatment level. A second condition that may be monitored by monitoring means 32 is tissue temperature generated by first and second thermal exchange component 28A and 28B. If, for example, monitoring means 32 senses a tissue temperature that is out of an acceptable range and poses a danger of injuring tissue around the knee, monitoring means 32 may communicate with the patient through display 30 to instruct removal of device 10 from the patient's knee.

For example, in one embodiment, monitoring means 32 may include a signal detector coupled to first stimulating means 16A and/or second stimulating means 16B for measuring the energy emission from first and second coils 26A and 26B. The signal detector may be designed so as to transmit a feedback signal to signal generator 12 for controlling the energy output. The actual electromagnetic energy field, or treatment dosage, that is transmitted from first and second stimulating means 16A and 16B may be measured directly by embedding the signal strength detector within the stimulating means. The signal level measured by the signal detector may then be sent to signal generator 12, where it may be used as a feedback control signal to control the output signals of the generator. If, at any time, monitoring means 32 detects a field strength outside of the desired range of the treatment mode, display 30 may display an audible, visible, tactile, or other type of alarm to inform the patient and/or physician of a malfunction in the treatment mode. Furthermore, if the measured field strength is at or above a level that poses a risk of danger, the feedback circuit of monitoring means 32 may stop the treatment to ensure that the patient is not harmed. As will be appreciated by one skilled in the art, monitoring means 32 may alternatively or additionally include a temperature sensor and associated feedback control to sense and control tissue temperature around the patient's knee.

As shown in FIG. 2, device 10 may be connected to a computer system 34 to allow the physician to program treatment modes into microcontroller 24. In this manner, the physician retains control over the type of treatment that the patient receives since device 10 may be designed such that only the physician is able to access and modify the programmed treatment modes. Through computer system 34, the physician may also monitor the treatment conditions to ensure that, for example, the correct field strength is being generated.

In order to make treatment with stimulation device 10 more convenient for both the physician and the patient, telemetry means 36 may be incorporated into the device. In general, telemetry allows for the remote measurement and reporting of information of interest to a remote system or operator. In addition, telemetry allows for the remote operation and control of a device by allowing the operator to remotely send instructions to or program the device.

With respect to stimulation device 10, telemetry means 36 enables the physician to remotely monitor the treatment as well as modify the treatment modes programmed into microcontroller 24. In this way, the physician has the ability to control and prescribe treatment modes without the requirement of a face-to-face consultation with the patient, thus making treatment of osteoarthritis more convenient for both the patient and the physician. In one embodiment, telemetry means 36 may operate using wireless communication, such as by utilizing a radio frequency system to implement the data link between the device and remote system. However, telemetry means 36 may alternatively transfer data over other media, such as a telephone line, a computer network, or via an optical link.

Figure 3:
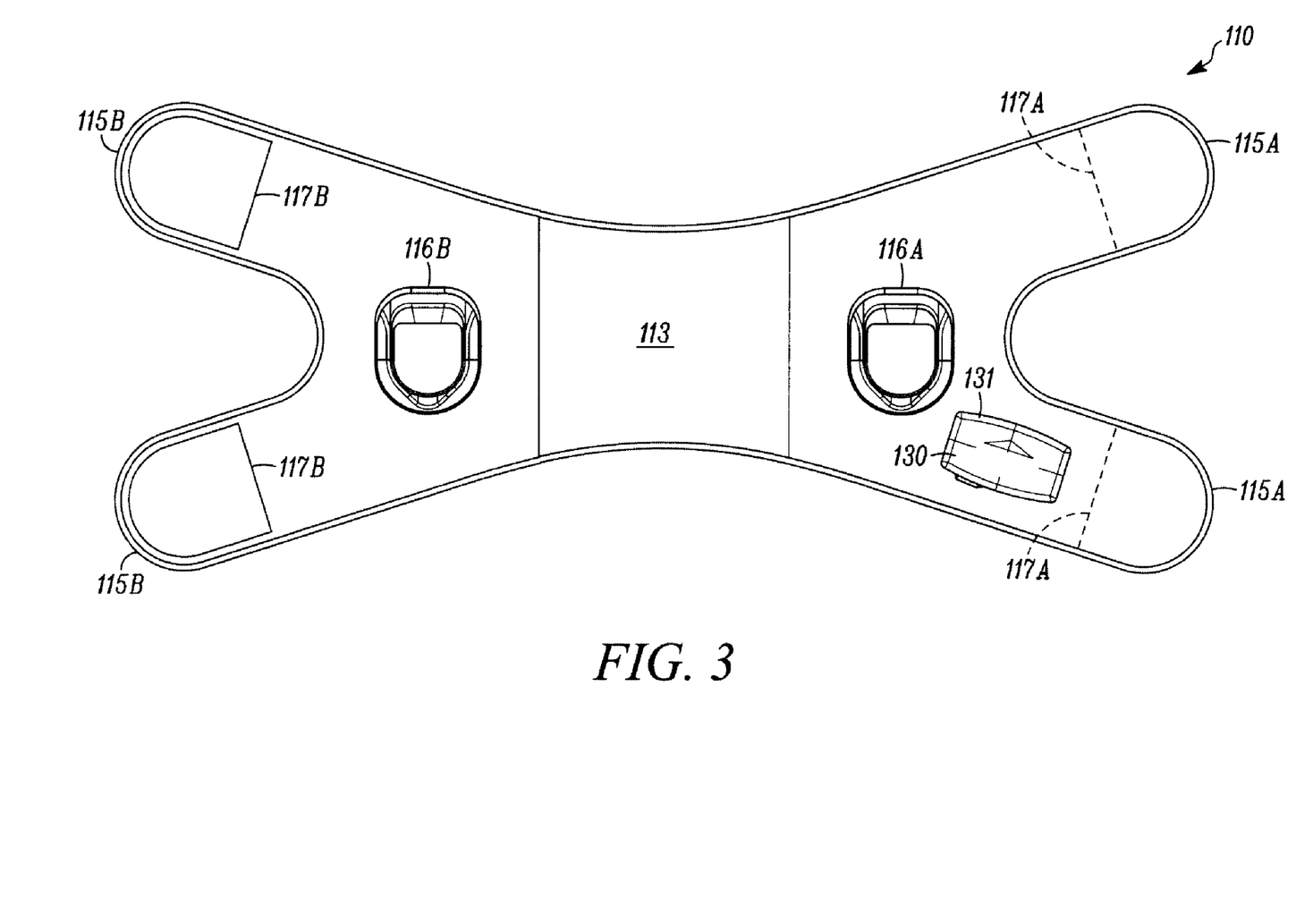
FIG. 3 is a front view of one embodiment of a stimulation device that is securable to a patient's knee for delivery of electromagnetic and thermal therapy.

Now that certain embodiments of the $EMT^2$ stimulation device have been generally described in reference to the block diagram illustration of FIG. 2, one exemplary embodiment of a stimulation device that may be worn by a patient for the treatment of osteoarthritis will be described. In particular, FIG. 3 illustrates a stimulation device 110, which generally includes a knee cuff 111, a housing 131 in which a signal generator and a power source are positioned, a first stimulating means 116A, a second stimulating means 116B, and a fastening means 117. The housing 131 can be positioned anywhere on the cuff 111. The device 110 alternatively also has a display 130 that can display one or more treatment parameters, such as the treatment mode or the amount of treatment time remaining in a therapy session. In the embodiment depicted in FIG. 3, the display 130 is located on the housing 131. Alternatively, the display 130 can be positioned in any location from which the display is visible to the user during use. Stimulation device 110 is a device for providing electromagnetic field stimulation and thermal therapy to a patient's body to promote healing. In particular, stimulation device 110 may provide pulsed electromagnetic field stimulation and thermal therapy (via first and second stimulating means 116A and 116B) to a knee joint suffering from the effects of osteoarthritis to promote healing of the knee. However, one skilled in the art will appreciate that various device embodiments disclosed herein may be useful to provide electromagnetic field stimulation and thermal therapy ($EMT^2$) to various other locations on a patient's body to promote healing or provide a therapeutic effect.

Knee cuff 111 includes main body portion 113, first set of strap members 115A, and second set of strap members 115B. First set of strap members 115A include first fastening members 117A, while second set of strap members 115B include second fastening members 117B. As will be discussed in the following paragraphs, first fastening members 117A are configured to mate with second fastening members 117B in order to removably couple first set of strap members 115A to second set of strap members 115B and thus, to secure knee cuff 111 to the patient's knee.

Figure 4A:
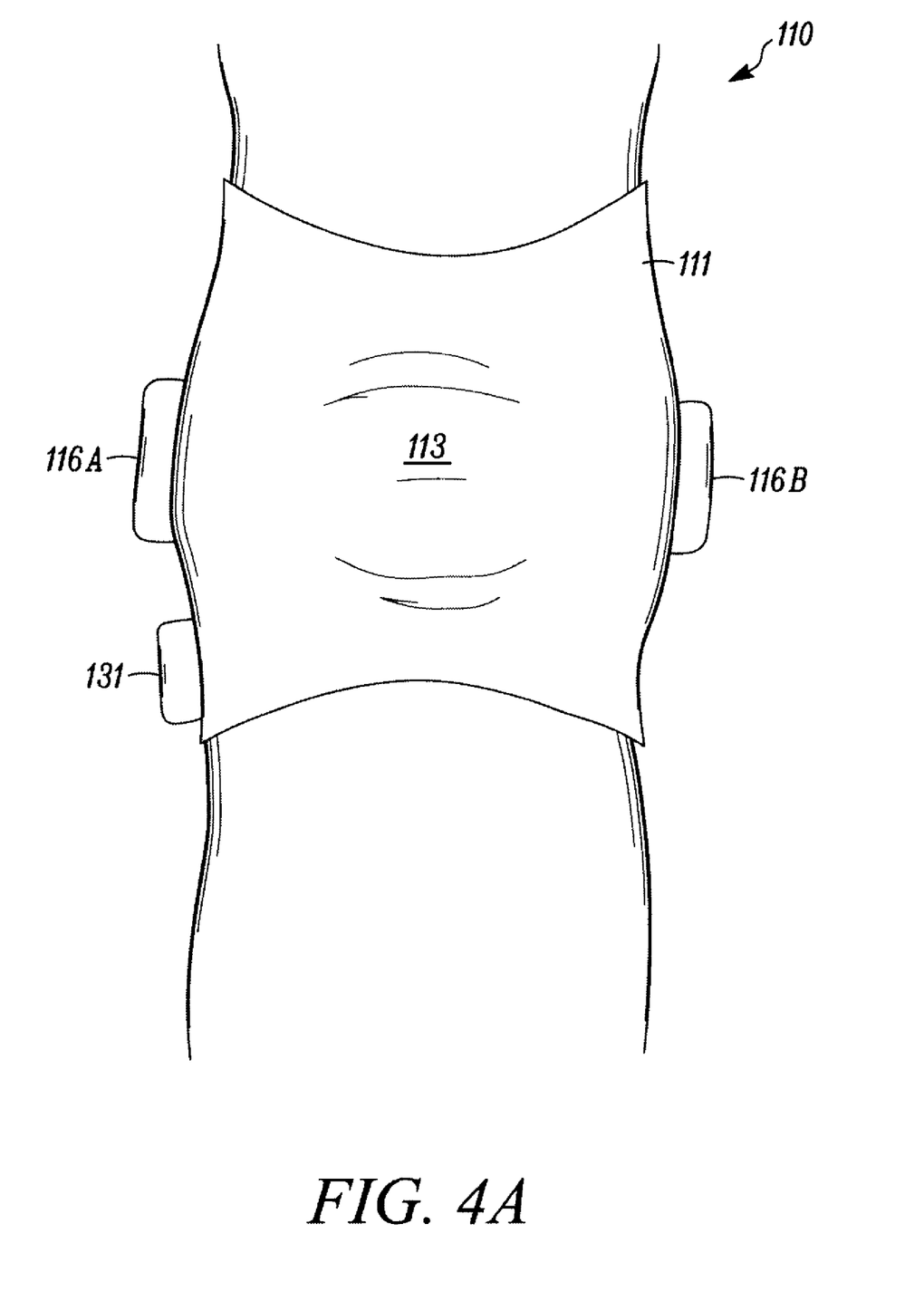
FIGS. 4A and 4B illustrate the stimulation device of FIG. 3 secured to the patient's knee.
Figure 4B:
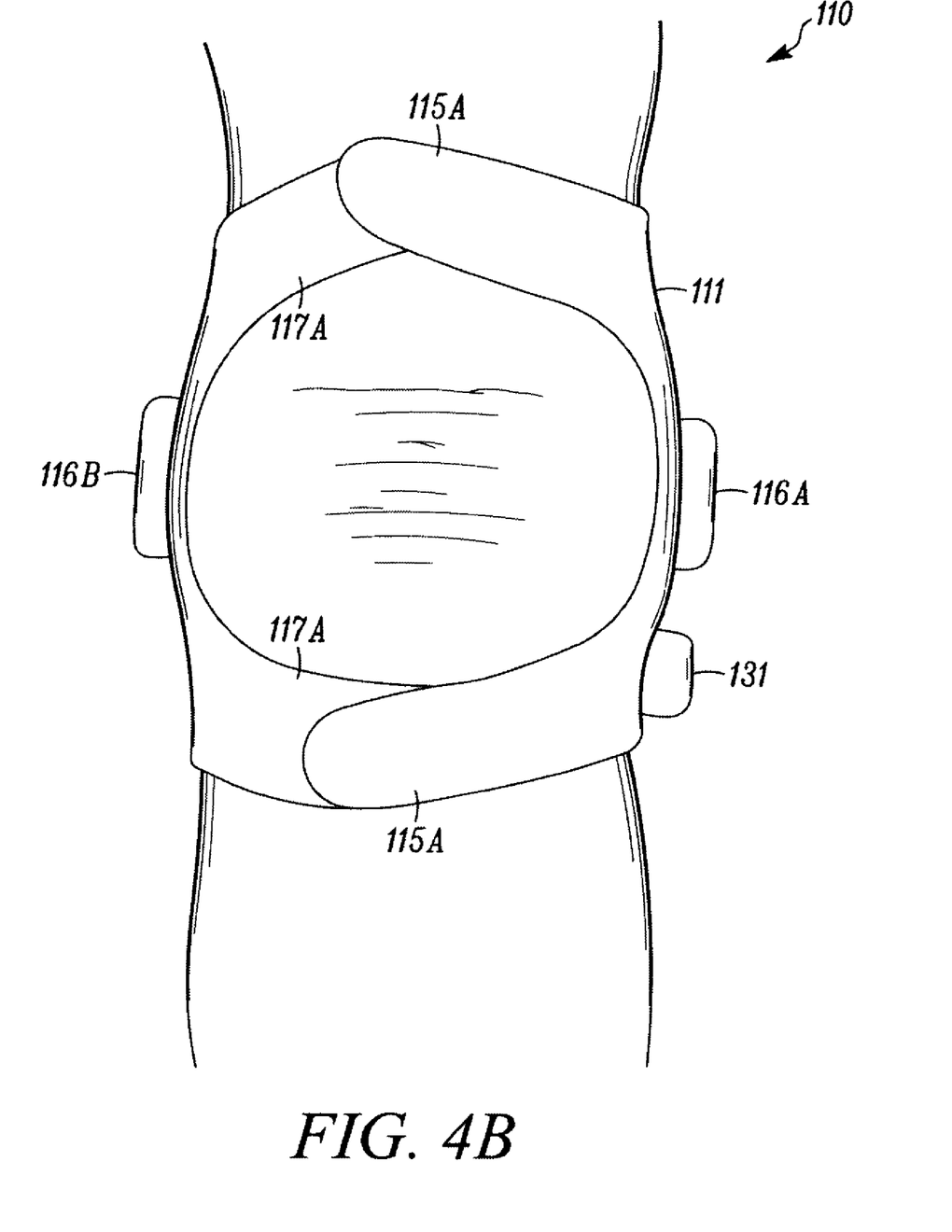

FIGS. 4A and 4B illustrate stimulation device 110 secured to the patient's knee, according to one embodiment. In particular, FIG. 4A illustrates a front side of the patient's knee, while FIG. 4B illustrates a back side of the knee. Knee cuff 111 of stimulation device 110 is wrapped around the knee such that first set of strap members 115A having first fastening members 117A overlap with second set of strap members 115B having second fastening members 117B to secure the cuff at the desired location on the knee. When properly secured to the knee, first stimulation means 116A is positioned at a lateral knee location, while second stimulating means 116B is positioned at a medial knee location. In one embodiment, first fastening members 117A and second fastening members 117B form a hook-and-loop fastening means, such as that commonly known as VELCRO®, wherein first fastening members 117A are the "hook" portions and second fastening members 117B are the "loop" portions. However, other means of fastening may be used including, but not limited to, buckles, snaps, and zippers. In alternate embodiments of knee cuff 111, no fastening means is used. Instead, the fabric forming the wrap is capable of being stretched and is able to hold itself in place due to the elasticity of the wrap.

Figure 5:
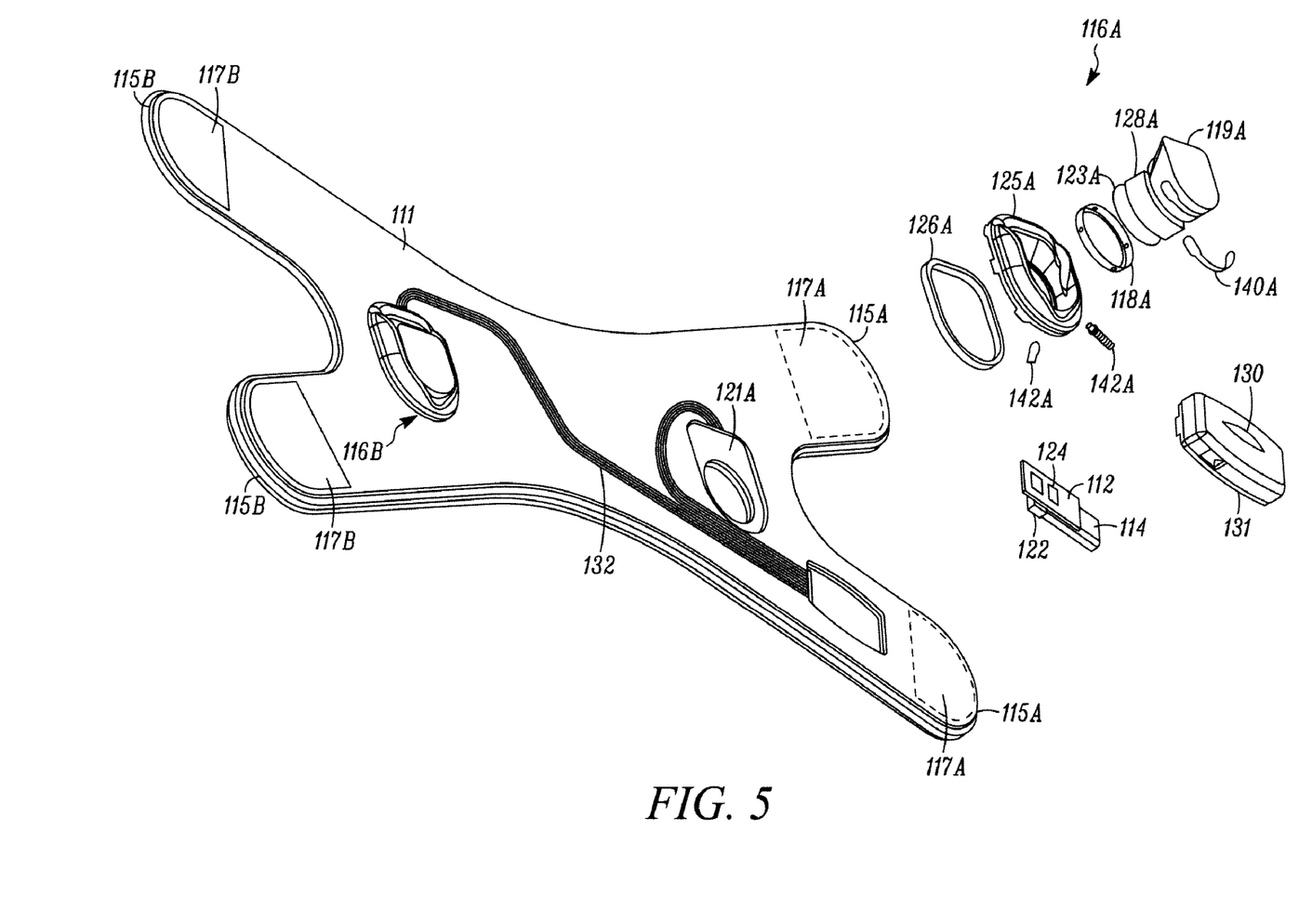
FIG. 5 is an exploded perspective view of the stimulation device of FIG. 3.

FIG. 5 is an exploded perspective view of stimulation device 110 according to a further embodiment. As shown in FIG. 5, first stimulating means 116A includes first coil 126A, first stimulating means holder 125A, first stimulating means holder base plate 121A, first thermal exchange component 128A, and first stimulating means housing 119A. First coil 126A of first stimulating means 116A is designed to be contained within the first stimulating means holder 125A. The first stimulating means holder base plate 121A provides a base for the first stimulating means holder 125A to attach to in order to be joined to the knee cuff by means of any one of such exemplary attachment mechanisms as, but not limited to, an irreversible snap-fit hook mechanism, ultrasonic welding, or glue. In one embodiment, the first stimulating means holder base plate 121A may be permanently attached to the knee cuff 111 by sewing, glue, or any known attachment means. First thermal exchange component 128A is designed to be contained within first thermal stimulating means housing 119A. Housing 119A may then be enclosed on a back side by a thin plastic barrier 123A formed from a material such as Tyvek®. The thin barrier 123A can be attached to the housing 119A by glue, heat seal, or a plastic snap-fit cover 118A. First thermal exchange component 119A is insertable into first stimulating means holder 125A, which is coupled to knee cuff 111 as shown in the embodiment depicted in FIG. 3.

Although not shown in an exploded view like first stimulating means 116A, second stimulating means 116B includes similar components in a similar configuration. Thus, the discussion focuses on first stimulating means 116A for purposes of example only, but applies equally to second stimulating means 116B. As a result, second stimulating means 116B includes similar components having similar reference numerals.

The signal generator 112 depicted schematically in FIG. 5 includes a voltage regulator 122 and a microcontroller 124, which control the signals transmitted through the wire harness 132 to first and second coils 126A and 126B to provide the pulsed electromagnetic field to the knee. The wire harness 132 is hidden within the different fabric layers of the knee cuff 111. Power source 114, which provides power to voltage regulator 122, is positioned in the same housing that contains the signal generator means 112. However, as discussed above, power source 114 may alternatively be positioned remotely from the signal generator means 112. In a further alternative embodiment, two power sources are provided: one for the signal generator and one for the thermal exchange component. In yet another embodiment, three power sources are provided: one for the signal generator and one for each of the thermal exchange components. In one embodiment, the power sources for the thermal exchange components are single-use heating mixtures that provide energy when exposed to air.

First and second coils 126A and 126B are either unipolar or bipolar electromagnets that generate a magnetic field when electrical current flows through them. The magnetic field is created by passing an electric current through first and second coils 126A and 126B, which are preferably formed from a long wire strand coiled around a core. The "pulsed" electromagnetic field may be created by programming microcontroller 124 to turn the electromagnetic field on and off at a rapid rate.

Although first and second thermal exchange components 128A and 128B are not required components, incorporating them into first and second stimulating means 116A and 116B, respectively, may provide beneficial treatment results. In particular, when used in combination with electromagnetic therapy, thermal therapy is helpful in treating the effects of osteoarthritis and improving patient compliance. However, one skilled in the art will appreciate that embodiments of stimulation device 110 that apply only thermal therapy, only electromagnetic therapy, or a combination of both therapies are possible. As a result, the stimulation devices described herein may be tailored to the particular needs of different patients.

Heat is a natural remedy that may be used to both relieve pain and reduce discomfort. This is accomplished by stimulating the patient's thermoreceptors which, in turn, aid in blocking the pain sensation from reaching the brain by relaxing deep muscles to reduce tenderness and pain. In order to attain a therapeutic heat transfer effect including increases in tissue temperature, blood flow, muscle lengthening, and metabolism, an intramuscular temperature of about 104 degrees F. (40 degrees Celsius) must be reached.

Numerous types of heat sources may be utilized to provide beneficial heat therapy in accordance with various implementations. For example, first and second thermal exchange components 128A and 128B may be multi-use cartridges that require the patient to 're-heat' the cartridges before every use, such as by placing the cartridges in the microwave. Alternatively, first and second thermal exchange components 128A and 128B may be one-time use cartridges that are designed to provide an irreversible exothermic reaction to provide a source of heat for a specified amount of time. In one embodiment, first and second thermal exchange components 128A and 128B are cartridges that contain iron, carbon, sodium chloride, sodium thiosulfate, and water. When the CLLHW compound is exposed to air, it undergoes an exothermic reaction that produces heat. In other embodiments, heat may be provided through: a resistive based heating source; selective insulation; or "warmth" radiated from the battery during operation. As will be appreciated by one skilled in the art, first and second thermal exchange components 128A and 128B may be heat sources designed such that they deliver heat therapy for any designated period of time ranging from a few minutes to the entire day. This designated period may or may not coincide with the electromagnetic field duration. In addition, first and second thermal exchange components 128A and 128B may be pulsed such that the heat therapy is not constant.

In one embodiment, power source 114 is a lithium-polymer battery, which may be either a single-use battery or a rechargeable, multi-use battery. If power source 114 is a rechargeable type battery, stimulation device 110 may be configured for attachment to a docking station for recharging the device. Alternatively, the docking station may be designed to receive only power source 114, which may be made removable from stimulation device 110. As one skilled in the art will appreciate, numerous other types of power sources may be used to provide the requisite power to stimulation device 110. For example, stimulation device 110 may be designed to create power from the patient's body movements. Alternatively, stimulation device 110 may be powered through a chemical reaction with heat being the by-product. In this case, the heat by-product may provide the heat therapy to the knee joint.

As shown in FIG. 5, stimulation device 110 further includes display 130 for displaying one or more treatment parameters, such as the treatment mode or the amount of treatment time remaining in a therapy session. Display 130 may utilize many different types of indicator means such as, for example, a light source, a heat-sensitive material that changes color (as a function of elapsed time), a digital timer, or sound repetition. In addition, display 130 may function together with a monitoring means in order to transmit an audio, visual, or tactile-type message to the patient in response to the monitoring means sensing, for example, an electromagnetic field strength that is outside of that defined by the treatment mode. In this instance, display 130 is useful to instruct the patient to remove the stimulation device or to call his or her physician.

Figure 6:
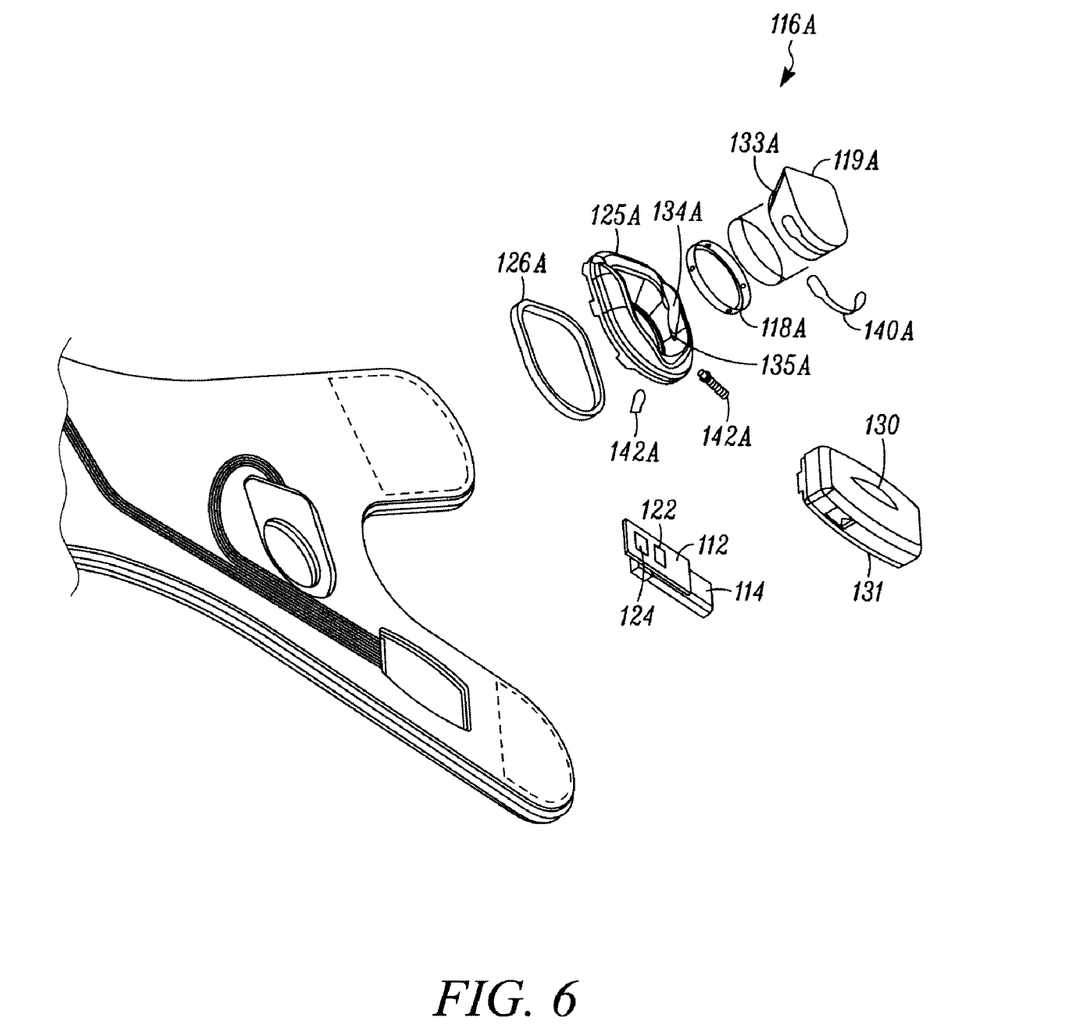
FIG. 6 is an enlarged exploded view of a portion of the stimulation device of FIG. 3.

FIG. 6 is an enlarged illustration of the exploded perspective view of FIG. 5, according to one embodiment. In this embodiment, the stimulating means housings 119A, 119B as depicted in FIG. 5 are insertable, replaceable units that can be easily and quickly inserted into and removed from the means holders 125A, 125B. In one embodiment, the stimulating means housings 119A, 119B have connections that, upon insertion into the holders 125A, 125B, couple with connections in the holders 125A, 125B to supply power to the housings 119A, 119B.

FIG. 6 depicts one embodiment of a stimulation device 110 with insertable stimulating means housings 119A, 119B. As shown in FIG. 6, the stimulation device 110 has a metal plate 140A in the stimulating means housing 119A and a first pair of stimulating means holder spring-loaded metal contacts 142A. When the stimulation device 110 is assembled as shown in the embodiment of FIG. 3, the metal plate 140A on the stimulating means housing 119A is used to make an electrical connection with a pair of spring-loaded metal contacts 142A in the first stimulating means holder 125A. The protrusions 133A on the stimulating means housing 119A can slide in and out of the grooves 134A on the stimulating means holder 125A and engage in the notches 135A to create a reversible mechanical snap-in feature that allows for secure insertion and removal of the housing 119A to the stimulating means holder 125A. In an alternative implementation, the metal plate 140A in the stimulating means housing 119A makes contact with the first pair of stimulating means holder magnets that are inserted into a first pair of magnet notches in first stimulating means holder 125A for securing the housing 119A to the first stimulating means holder 125A. In a further alternative, instead of a metal plate, the stimulation device 110 can have a pair of stimulating means magnets and a corresponding pair of stimulating means holder magnets.

The first pair of stimulating means holder spring-loaded metal contacts 142A are coupled to a corresponding pair of signal lines (not shown) in communication with signal generator 112. When first stimulating means housing 119A is positioned within first stimulating means holder 125A, the electrical connection between the metal plate 140A and the corresponding first pair of stimulating means holder spring-loaded metal contacts 142A creates a closed circuit that electrically couples first stimulating means 116A to signal generator 112. As a result, signal generator 112 is able to communicate with first stimulating means 116A to deliver the prescribed treatment signals defined by the treatment mode programmed into microcontroller 124.

The embodiment of stimulation device 110 illustrated in FIGS. 3-6 is a two coil arrangement with one coil on either side of the knee for generating the PEMF therapy. In general, voltage regulator 122 is used to provide a constant supply voltage to signal generator 112, and first and second stimulating means 116A and 116B. Microcontroller 124 triggers first and second coils 126A and 126B, thereby generating accurate pulses at a particular triggering and switching frequency defined by the designated treatment mode stored in the microcontroller. The triggering frequency is defined as the rate at which a set number of pulses occur. The switching frequency is the fundamental frequency of the individual pulses. Another parameter called the switching duty cycle is defined as the ratio of the pulse width over the switching period. The voltage of the pulses is equivalent to the amplitude of the PEMF therapy.

The required penetration depth of the pulsed electromagnetic field generated by signal generator 112 and first and second stimulating means 116A and 116B may vary depending upon, for example, the size of the patient's knee region. However, for an adult patient, the penetration depth is generally in the range of about 1 cm to about 5 cm. Alternatively, the penetration depth is in the range of about 2 cm to about 4 cm. In a further alternative, the penetration depth ranges from about 2 cm to about 2.5 cm. This "penetration depth" parameter is necessary in order to estimate the magnetic field intensity needed to provide the therapy, which ultimately determines the power requirement of power source 114.

In general, the magnetic field intensity generated by a coil is measured in terms of Tesla (T) and has the following approximate relationship with current flowing through the coil:

$$B = \frac{\mu_0 n I R^2}{2(R^2 + x^2)^{3/2}} \Rightarrow I \frac{2B(R^2 + x^2)^{3/2}}{\mu_0 n R^2}$$

where "B" is the magnetic field produced by the coil, "I" is the current through the coil, "R" is the radius of the coil, and "x" is the penetration depth of the PEMF.

According to one embodiment, the magnetic field strength B applied to the target body part of the patient ranges from about 10 µT to about 2,000 µT. Alternatively, the magnetic field strength B ranges from about 20 µT to about 100 µT. In a further alternative, the magnetic field strength B ranges from about 30 µT to about 50 µT. In yet another alternative, the magnetic field strength B is about 40 µT. According to one embodiment, the magnetic field produced by the coil is applied perpendicular to the coil.

In one implementation, the magnetic field is applied into the knee for a distance ranging from about 1 cm to about 5 cm into the knee. Alternatively, the magnetic field is applied for a distance ranging from about 2 cm to about 4 cm into the knee. In a further alternative, the magnetic field is applied to a distance ranging from about 2 cm to about 2.5 cm into the knee.

The coil, in accordance with one embodiment, has 20 turns of a 24 AWG wire around a core with a radius of about 2 centimeters with a pulsed current 712 mA. Alternatively, the coil has 65 turns of a 28 AWG wire around a core with a radius of 1.5 cm with a pulsed current of 339 mA.

While a single-coil configuration is possible and within the intended scope of this application, the two-coil configuration uses about 20 times less power than the single-coil configuration because it requires a significantly smaller amount of energy to penetrate both the lateral and medial side of the knee. Furthermore, embodiments having more than two coils are also contemplated.

In one embodiment, the PEMF therapy is applied for period ranging from about 30 minutes to about 4 hours. Alternatively, the PEMF therapy is applied for a period ranging from about 1 hour to about 3 hours. In a further alternative, the therapy is applied from about 1.5 to about 2.5 hours. In yet another alternative, the therapy is applied for about 2 hours. Further, the optimal treatment window may vary depending upon many factors, including, but not limited to, the field intensity provided to the knee, the severity of the osteoarthritis in the knee, and the physical dimensions of the knee.

According to one implementation, the triggering frequency ranges from about 1 Hz to about 100 Hz. Alternatively, the triggering frequency ranges from about 5 Hz to about 50 Hz. In a further alternative, the triggering frequency ranges from about 10 Hz to about 20 Hz. In yet another alternative, the triggering frequency is about 15 Hz.

In accordance with one embodiment, the switching frequency ranges from about 50 Hz to about 100 kHz. Alternatively, the switching frequency ranges from about 300 Hz to about 70 kHz. In a further alternative, the switching frequency ranges from about 2 kHz to about 4 kHz. In yet another alternative, the switching frequency is about 3 kHz.

In general, in order to achieve the optimal therapeutic effect with the PEMF, a triggering frequency in the range of about 15 Hz and a switching frequency in the range of about 3 kHz are desirable, although other triggering and switching frequencies are also contemplated.

As one skilled in the art will appreciate based upon the above disclosure, stimulation device 110 does not require connection to any external hardware while delivering the prescribed therapy. Thus, stimulation device 110 is portable, and is designed such that it may be worn by the patient during their normal daily activities without discomfort. Knee cuff 111 may be both ergonomically designed and cosmetically appealing to increase patient compliance with wearing the device.

First and second stimulating means 116A and 116B may be designed as complete or partial disposable units that may be discarded and replaced after a predetermined number of treatments. For example, stimulating means housing 119A, which may include first thermal exchange component 128A and/or first coil 126A, may be removed from stimulation means holder 125A and disposed of by the patient upon expiration. Optionally, display 130 may instruct the patient when the units have expired and require replacement. The disposability feature of first and second stimulating means 116A and 116B may be advantageous because if one or more of the stimulating means stops functioning properly, it is only necessary to replace those components and not the entire stimulation device.

Figure 7:
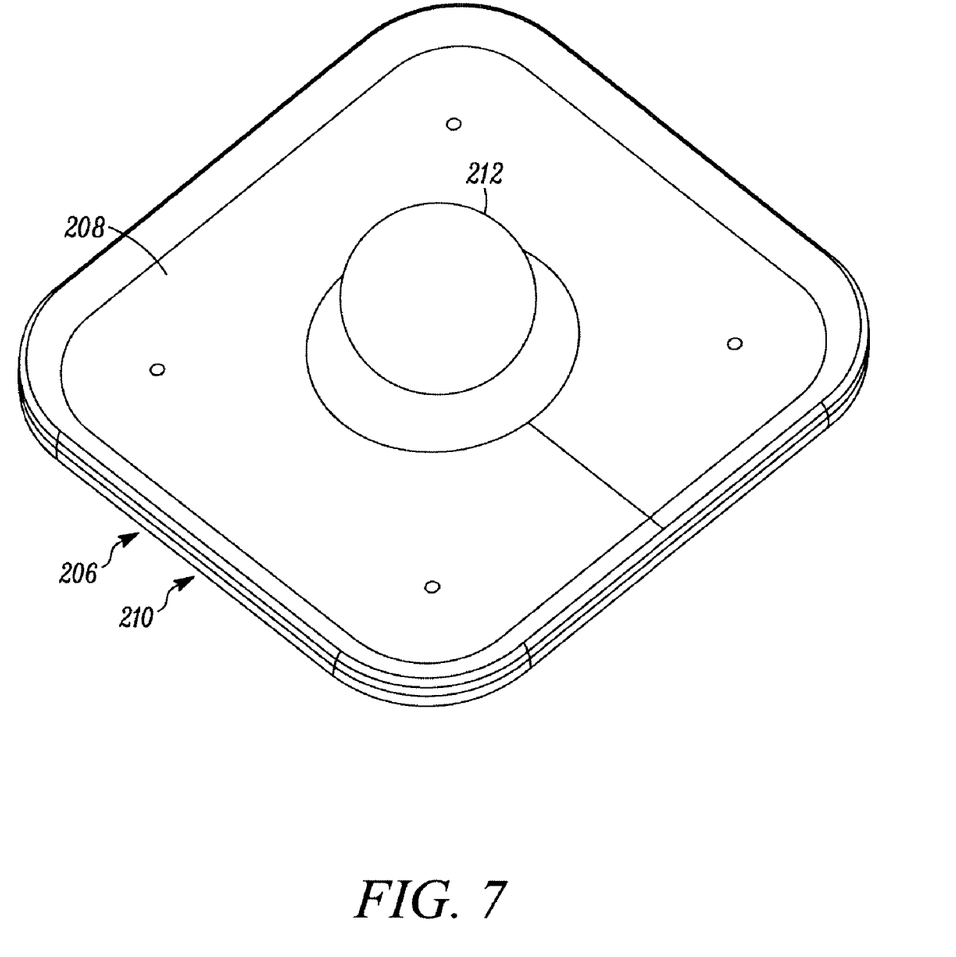
FIG. 7 is a perspective view of one embodiment of a stimulation device in the form of a patch that is securable to a patient's body for delivery of electromagnetic and thermal therapy.

Another exemplary embodiment of an $EMT^2$ stimulation device is depicted in FIG. 7. The device 200 shown in FIG. 7 has a PEMF generation component 202 and a thermal exchange component 204. The PEMF generation component 202 is positioned between a first exterior layer 206 and a second exterior layer 208. According to one embodiment, the first layer 206 has an adhesive component 210 on at least a portion of the side of the layer external to the device 200. The adhesive component 210 is any known adhesive that allows for attaching the device 200 to the patient's skin.

In accordance with one implementation, the device 200 also has a power source (not shown) positioned in an external casing 212 positioned on the second layer 208. In a further embodiment, certain electronic components can be positioned in the casing 212.

Alternatively, the device 200 has two power sources (not shown)—one for the PEMF generation component 202 and one for the thermal exchange component 204. Two different power sources can help to maximize battery life. Alternatively, one power source is provided for both the PEMF generation component 202 and the thermal exchange component 204. In a further embodiment, one power source is provided for the PEMF generation component 202, and the thermal exchange component 204 in this embodiment requires no power source, as explained in further detail below. According to one implementation, the single power source or both power sources are positioned in the external casing 212. Alternatively, the single power source or both power sources are positioned between the first layer 206 and the second layer 208. In a further alternative, one power source is positioned in the external casing 212 and one power source is positioned in between the first 206 and second 208 layers.

In one embodiment, one or both of the power sources are a single-use or disposable power source. Alternatively, the one or more power sources can be reusable or permanent power sources. In a further alternative, the power source is any known power source for use with a PEMF stimulation device and/or a thermal exchange component.

In one embodiment, the device 200 is a single-use patch-like device. Alternatively, the device 200 is a reusable device. As shown, the device 200 has a square shape. Alternatively, the device 200 can have a circular or round shape or any other known shape. For example, in one embodiment, the device 200 may have any shape that maximizes attachment to the patient's skin and patient comfort.

In this embodiment, the PEMF generation component 202 is a coil configured to generate the pulsed electromagnetic field. Alternatively, the PEMF generation component 202 can be any known component for generating a PEMF.

According to one implementation, the thermal exchange component 204 is a heat source such as, for example, a component having an exothermic chemical mixture. For example, the heat source in one embodiment is a mixture containing iron powder, water, activated charcoal, and salt that oxidizes in air to generate heat. One commercial example of such a mixture can be found in hand warming products sold by HeatMax®, which is located in Dalton, Ga. Another example of a heat source that can be used with the present embodiment is a mixture containing super-cooled sodium acetate. Yet another example is a mixture containing calcium chloride or magnesium sulfate and water. In a further alternative, the thermal exchange component can be any known component or device for generating heat.

In accordance with one implementation in which the thermal exchange component 204 is a heat source utilizing an exothermic chemical mixture, the component 204 does not require a power source. That is, the chemical mixture generates the exothermic reaction without the need for any battery or any other kind of power source.

Alternatively, the thermal exchange component 204 is a cooling source such as, for example, a component having an endothermic chemical mixture. For example, the cooling source can be a mixture containing ammonium nitrate and water. In a further alternative, the thermal exchange component 204 can be any known component for providing a temperature reduction.

In one implementation, the first and second exterior layers 206, 208 are flexible or pliable layers. The layer pliability or flexibility can, according to one embodiment, facilitate attachment of the device 200 to the patient's skin. In one alternative embodiment, one or both of the exterior layers can be gas permeable. In a further alternative, one or both of the exterior layers are permeable to oxygen. The layers 206, 208 can consist of a biocompatible membrane such as, for example, the Tegaderm™ and Medipore™ products available from 3M™ Company, located in St. Paul, Minn.

According to one embodiment, the adhesive component 210 is a hypoallergenic adhesive. In a further alternative implementation in which one or both of the exterior layers 206, 208 are gas permeable, the adhesive component 210 is a porous adhesive that allows gas to pass through the adhesive and the gas permeable layer.

It is understood that this device 200 can be used to treat any joint or any other body part that might benefit from treatment with PEMF and thermal exchange. In one embodiment, the target area is the knee. It is further understood that more than one device 200 could be used to treat a target area. The device 200 can be used to relieve osteoarthritis pain and increase range of motion.

One skilled in the art will appreciate that although the devices and methods have been described in reference to only a few embodiments of a stimulation device, these embodiments are provided for purposes of example and not limitation. Accordingly, numerous other embodiments are possible and within the intended scope.

What is claimed is:

1. A portable, non-invasive device for providing therapeutic treatment to a knee joint to promote healing of the knee joint, the device comprising:
a multi-usage knee cuff positionable around the knee joint, the multi-usage knee cuff comprising:
an electromagnetic therapy portion, comprising:
a signal generator for generating pulsed signals based upon a selected treatment mode;
a controller for storing the treatment mode and communicating the treatment mode to the signal generator; and
an electromagnetic stimulator configured to receive the signals from the signal generator and generate an electromagnetic field within the knee joint, the electromagnetic stimulator comprising:
a medial coil configured to receive a signal from the signal generator and to generate an electromagnetic field within a medial area of the knee joint; and
a lateral coil configured to receive a signal from the signal generator and to generate an electromagnetic field within a lateral area of the knee joint;
a temperature-based therapy portion, comprising:
a thermal exchange component configured to provide temperature-based therapy to the knee joint, the thermal exchange component comprising:
a medial single-use therapy unit configured to provide temperature-based therapy to a medial area of the knee joint; and
a lateral single-use therapy unit configured to provide temperature-based therapy to a lateral area of the knee joint; and
a display for displaying one or more treatment parameters.

2. The device of claim 1, further comprising a rechargeable battery coupled to the signal generator.

3. The device of claim 1, further comprising a first power source coupled to the signal generator, and a second, different power source coupled to the thermal exchange component.

4. The device of claim 1, wherein the thermal exchange component is a heat source configured to provide heat therapy to the knee joint.

5. The device of claim 1, further comprising a disposable stimulator housing comprising at least one of the electromagnetic stimulator and the thermal exchange component, wherein the disposable stimulator housing is configured to be mechanically coupled to a receptacle on the multi-usage knee cuff.

6. The device of claim 1, further comprising an electromagnetic field monitor configured to monitor the electromagnetic field generated by the electromagnetic stimulator; and
a feedback circuit between the electromagnetic field monitor and the controller for adjusting the treatment mode if a sensed electromagnetic field is outside of a specified range.

7. The device of claim 1, wherein the thermal exchange component is a cooling source configured to provide cold therapy to the knee joint.

8. The device of claim 1, wherein the thermal exchange component is configured to provide pulsed temperature-based therapy to the knee joint.

9. The device of claim 1, wherein the electromagnetic stimulator is configured to generate the electromagnetic field within the knee joint that coincides in duration with the temperature-based therapy to the knee joint.

10. The device of claim 1, wherein the electromagnetic stimulator is configured to generate the electromagnetic field within the knee joint that does not coincide in duration with the temperature-based therapy to the knee joint.

11. The device of claim 5, wherein the disposable stimulator housing, when mechanically coupled to the receptacle on the multi-usage knee cuff, is configured to enable the electromagnetic stimulator to generate the electromagnetic field within the knee joint.

12. The device of claim 1, further comprising a temperature monitor for monitoring a tissue temperature; and
a feedback circuit between the temperature monitor and the controller for adjusting the treatment mode if a tissue temperature is outside of a specified range.

13. A method for providing therapeutic treatment to a knee joint, the method comprising:
positioning a multi-usage knee cuff around the knee joint, the multi-usage knee cuff comprising:
an electromagnetic stimulator configured to generate an electromagnetic field within the knee joint, wherein the electromagnetic stimulator includes a medial coil and a lateral coil; and
a thermal exchange component configured to provide temperature-based therapy to the knee joint, wherein the thermal exchange component include a medial single-use therapy unit and a lateral single-use therapy unit;
wherein the positioning the multi-usage knee cuff includes:
positioning the medial coil to generate an electromagnetic field within a medial area of the knee joint;
positioning the lateral coil to generate an electromagnetic field within a lateral area of the knee joint;
positioning the medial single-use therapy unit to provide temperature-based therapy to a medial area of the knee joint; and
positioning the lateral single-use therapy unit to provide temperature-based therapy to a lateral area of the knee joint;
generating signals with a signal generator based upon a selected treatment mode, the treatment mode stored in a controller;
communicating the signals to the electromagnetic stimulator;
generating a pulsed electromagnetic field within the medial area of the knee joint, and separately, within the lateral area of the knee joint using the electromagnetic stimulator;
generating a therapeutic temperature-related treatment within the medial area of the knee joint, and separately, within the lateral area of the knee joint using the thermal exchange component; and
displaying one or more treatment parameters on a display coupled to the controller.

14. The method of claim 13, wherein generating the therapeutic temperature-related treatment includes generating therapeutic heat treatment using an exothermic reaction.

15. The method of claim 13, further comprising monitoring the electromagnetic field generated by the electromagnetic stimulator and adjusting the treatment mode if a sensed electromagnetic field is outside of a specified range.

16. The method of claim 13, further comprising providing power to the signal generator using body movement.

17. The method of claim 13, further comprising mechanically coupling the thermal exchange component to a receptacle on the multi-usage knee cuff.

18. The method of claim 17, further comprising enabling the generating the pulsed electromagnetic field using the mechanically coupling the thermal exchange component to the receptacle on the multi-usage knee cuff.

19. The method of claim 13, wherein the generating the therapeutic temperature-related treatment includes generating therapeutic cold treatment.

20. The method of claim 13, wherein the generating the therapeutic temperature-related treatment includes generating pulsed therapeutic temperature-related treatment.

21. The method of claim 13, wherein the generating the pulsed electromagnetic field coincides in duration with the generating the therapeutic temperature-related treatment.

22. The method of claim 13, further comprising monitoring a tissue temperature and adjusting the treatment mode if the tissue temperature is outside of a specified range.

23. A method for providing therapeutic treatment to a knee joint, the method comprising:
providing a multi-usage knee cuff positionable around the knee joint, the multi-usage knee cuff comprising:
an electromagnetic stimulator configured to generate an electromagnetic field within the knee joint, the electromagnetic stimulator comprising a medial coil and a lateral coil; and
a thermal exchange component configured to provide temperature-based therapy to the knee joint, the thermal exchange component comprising a medial single-use therapy unit and a lateral single-use therapy unit;
generating signals with a signal generator based upon a selected treatment mode, the treatment mode stored in a controller;
communicating the signals to the electromagnetic stimulator;
generating a pulsed electromagnetic field using the medial coil and the lateral coil;
generating a therapeutic temperature-related treatment using the medial single-use therapy unit, and separately, within the lateral area of the knee joint using the lateral single-use therapy unit; and
displaying one or more treatment parameters on a display coupled to the controller.

24. The method of claim 23, further comprising mechanically coupling the thermal exchange component to a receptacle on the multi-usage knee cuff.

25. The method of claim 24, further comprising enabling the generating the pulsed electromagnetic field using the mechanically coupling the thermal exchange component to the receptacle on the multi-usage knee cuff.

* * * * *